United States Patent
Hari et al.

(10) Patent No.: US 10,946,308 B2
(45) Date of Patent: *Mar. 16, 2021

(54) ENZYMATIC METHOD FOR EXTRACTION AND PURIFICATION OF PHYTOCANNABINOIDS

(71) Applicant: Bright Green Corporation, Wilmington, DE (US)

(72) Inventors: V. Hari, Orlando, FL (US); John Stockwell, Leamington (CA)

(73) Assignee: BRIGHT GREEN CORPORATION

( * ) Notice: Subject to any disclaimer, the term of this patent is extended or adjusted under 35 U.S.C. 154(b) by 0 days.

This patent is subject to a terminal disclaimer.

(21) Appl. No.: 16/510,245

(22) Filed: Jul. 12, 2019

(65) Prior Publication Data

US 2020/0016509 A1 Jan. 16, 2020

Related U.S. Application Data

(60) Provisional application No. 62/696,934, filed on Jul. 12, 2018.

(51) Int. Cl.

| B01D 11/02 | (2006.01) |
|---|---|
| B01D 15/08 | (2006.01) |
| B01D 39/06 | (2006.01) |
| B01D 3/10 | (2006.01) |
| A61K 36/16 | (2006.01) |
| A61K 36/185 | (2006.01) |
| A61K 36/268 | (2006.01) |
| A61K 36/906 | (2006.01) |
| A61K 36/9066 | (2006.01) |

(52) U.S. Cl.
CPC .......... *B01D 11/0288* (2013.01); *A61K 36/16* (2013.01); *A61K 36/185* (2013.01); *A61K 36/268* (2013.01); *A61K 36/906* (2013.01); *A61K 36/9066* (2013.01); *B01D 3/10* (2013.01); *B01D 11/0203* (2013.01); *B01D 11/0211* (2013.01); *B01D 15/08* (2013.01); *B01D 39/06* (2013.01)

(58) Field of Classification Search
CPC ............ B01D 11/0288; B01D 11/0203; B01D 39/06; B01D 3/10; B01D 15/08; B01D 11/0211; B01D 1/00; B01D 9/00; B01D 9/0018; B01D 9/0059; B01D 11/0261; B01D 11/028; B01D 15/12; B01D 15/125; B01D 36/00; B01D 36/02; B01D 39/2055; B01D 39/2058; A61L 2202/21; A61L 2/005; A61L 2/0011; A61L 2/0017; A61L 2/0047; A61L 2/0064; A61L 2/02; A61L 2/022; A61L 2/10; A61L 2/12; A61L 2/202; C12N 11/18; C11B 1/02; C11B 1/025; C11B 1/04; C11B 1/10; C11B 1/104; C11B 1/108; C11B 3/00; C11B 3/001; C11B 3/003; C11B 3/005; C11B 3/006; C11B 3/008; C11B 3/08; C11B 3/12; C11B 3/16; A61K 36/00; A61K 36/16; A61K 36/185; A61K 36/268; A61K 36/53; A61K 36/532; A61K 36/62; A61K 36/896; A61K 36/906; A61K 36/9066; F26B 5/06

USPC ............ 210/634, 638, 748.1, 760, 770, 774; 424/725, 728, 752, 756, 764, 773, 774, 424/778; 554/8, 20, 21, 22, 175, 206; 435/132, 175, 267, 271

See application file for complete search history.

(56) References Cited

U.S. PATENT DOCUMENTS

| 8,445,034 | B1 * | 5/2013 | Coles, Jr. | A61K 31/192 424/725 |
|---|---|---|---|---|
| 9,044,390 | B1 * | 6/2015 | Speier | A61K 36/00 |
| 9,956,498 | B1 * | 5/2018 | Tucker | B01D 3/36 |
| 10,557,105 | B1 * | 2/2020 | Tran | C11B 1/104 |
| 10,675,264 | B2 * | 6/2020 | Green | A61K 31/045 |
| 2013/0203849 | A1 * | 8/2013 | Ben Yehuda | A23L 19/105 514/557 |
| 2016/0279073 | A1 * | 9/2016 | Donsky | A61K 47/36 |
| 2016/0376263 | A1 * | 12/2016 | Patron | C07D 413/14 514/784 |
| 2017/0266153 | A1 * | 9/2017 | Levy | A61K 31/352 |
| 2018/0153196 | A1 * | 6/2018 | Rao | A23L 5/23 |
| 2018/0184705 | A1 * | 7/2018 | Wasserman | A24B 15/167 |
| 2018/0344785 | A1 * | 12/2018 | Robertson | A61K 36/185 |
| 2018/0369192 | A1 * | 12/2018 | Green | A61K 31/352 |
| 2019/0032099 | A1 * | 1/2019 | Johnston | C12P 19/14 |
| 2019/0083418 | A1 * | 3/2019 | Guy | A61K 31/352 |
| 2019/0192993 | A1 * | 6/2019 | Levy | B01D 11/0265 |
| 2019/0246591 | A1 * | 8/2019 | Leo | A01K 67/033 |
| 2020/0061136 | A1 * | 2/2020 | Venturini Del Greco | A61K 31/352 |

OTHER PUBLICATIONS

Munish Puri et al, "Enzyme-assisted extraction of bioactives from plants.", published in "Trends in Biotechnology", vol. 30, Issue No. 1, Jan. 2012. (Year: 2012).*

* cited by examiner

*Primary Examiner* — Joseph W Drodge
(74) *Attorney, Agent, or Firm* — Carlson, Gaskey & Olds, P.C.

(57) ABSTRACT

An example method of extracting phytocannabinoids from plants includes obtaining plant parts from at least one plant, the at least one plant including one or more of *Cannabis*, Turmeric, Ginseng, Ginkgo, Ginger, Vinca, and Bacopa. The plant parts are cooled, and are incubated in an incubation mixture of cellulose, pectinase, amylase, and proteinase dissolved in a buffer. The incubation mixture is evaporated in an evaporation chamber to obtain a phytocannabinoid extract.

17 Claims, No Drawings

ENZYMATIC METHOD FOR EXTRACTION AND PURIFICATION OF PHYTOCANNABINOIDS

CROSS-REFERENCE TO RELATED APPLICATIONS

This application claims priority to U.S. Provisional Application No. 62/696,934, which was filed on Jul. 12, 2018, and is incorporated herein by reference.

BACKGROUND

The present disclosure relates to phytocannabinoids, and more particularly to an enzymatic method for extraction and purification of phytocannabinoids using plant cell wall and cell content digesting enzymes.

Plant cells are bounded by rigid cell walls made of cellulose along with other minor polymers. Individual cells are held together with adjacent cells by pectin. This presents challenges for extracting phytocannabinoids from plants.

SUMMARY

An example method of extracting phytocannabinoids from plants includes obtaining plant parts from at least one plant, the at least one plant including one or more of *Cannabis*, Turmeric, Ginseng, Ginkgo, Ginger, Vinca, and Bacopa. The plant parts are cooled, and are incubated in an incubation mixture of cellulose, pectinase, amylase, and proteinase dissolved in a buffer. The incubation mixture is evaporated in an evaporation chamber to obtain a phytocannabinoid extract.

The embodiments, examples, and alternatives of the preceding paragraph, the claims, or the following description and drawings, including any of their various aspects or respective individual features, may be taken independently or in any combination. Features described in connection with one embodiment are applicable to all embodiments, unless such features are incompatible.

DETAILED DESCRIPTION

The present disclosure describes a novel method for extraction and purification of phytochemicals from *Cannabis sativa* and its sub species, varieties, hybrids, bio and ecotypes, by enzymatic digestion of cell walls, membranes and contents of cells, which results in the release of phytocannabinoids into the medium. The cannabinoid oil, which is insoluble in aqueous media, is extracted by, e.g., microwave assisted solvent extraction or super critical $CO_2$ extraction. The protocol makes use of the known structural features of plant cells which are held together by cellulose, pectin and other polymers.

When plant parts are chopped up or powdered and incubated in cellulase, pectinase, amylase and proteinases by vacuum infiltration, the cell walls, membranes, protein, and starch are digested and the contents are released into the incubating medium. Microwave assisted extraction in the presence of solvents aids efficient, rapid extraction of the released phytochemicals.

In an example embodiment, the method includes gathering plant organs such as leaves, flowers, roots and other plant parts. Those parts are sanitized by being washed, exposed to UV radiation or ozonolysis and then cut into small pieces or powdered. When cut, a preferred size of the pieces is about 1 square inch. If the sanitized plant organs are powdered, it is preferably done in the presence of dry ice (solid $CO_2$).

The next step involves incubating the pieces or powder in a mixture of cellulase, pectinase, amylase and proteinase, dissolved in a neutral buffer containing no more than 0.1 percent surfactant after vacuum infiltration of the plant tissue into the incubation medium. The mixture of the plant tissue and the incubation medium is incubated for up to 24 hours on a shaker platform that vigorously shakes the mixture. The incubated mixture is heated at a temperature around 45-50 degrees Celsius in an evaporation chamber to evaporate water from the mixture without causing evaporation of volatile oils. The resulting residue is extracted using ethanol, olive oil, coconut oil or hemp oil. Microwave assisted extraction is used in some embodiments to maximize cannabinoid extraction from cannabis or other phytochemicals even in situations where the cannabinoids are present in low concentrations. In other embodiments, the cell digested incubation mixture is directly subjected to super critical $CO_2$ extraction without using microwave assisted rapid extraction.

The extract resulting from the disclosed technique may be a starting point for industrial-type vacuum distillation or preparative chromatographic separations, such as high performance liquid chromatography (HPLC) for purifying and separating individual, different cannabinoid fractions.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. A method of extracting phytocannabinoids from plants, comprising:
    obtaining plant parts from at least one plant, the at least one plant including one or more of *Cannabis*, Turmeric, Ginseng, Ginkgo, Ginger, Vinca, and Bacopa;
    cooling the plant parts;
    incubating the plant parts in an incubation mixture of cellulase, pectinase, amylase, and proteinase dissolved in a buffer;
    evaporating the incubation mixture in an evaporation chamber; and
    extracting a phytocannabinoid extract from the evaporated incubation mixture.

2. The method of claim 1, wherein the buffer is a neutral buffer that contains no more than 0.1% surfactant.

3. The method of claim 1, comprising sanitizing the plant parts, said sanitizing comprising performing at least one of washing the plant parts, subjecting the plant parts to ultraviolet irradiation, and subjecting the plant parts to ozonolysis.

4. The method of claim 1, comprising shaking the incubation mixture during said incubating.

5. The method of claim 1, wherein said cooling the plant parts comprises freezing the plant parts using dry ice.

6. The method of claim 1, comprising, during said cooling and prior to said incubating, cutting the plant parts into pieces of not more than 1 inch in length in any direction.

7. The method of claim 1, comprising, during said cooling and prior to said incubating, reducing plant parts to a plant powder.

8. The method of claim 1, wherein the plant parts are plant organs including one or more of leaves, flowers, and roots.

9. The method of claim 1, wherein said evaporating the incubation mixture in an evaporation chamber comprises heating the incubation mixture at 45-50° Celsius in the evaporation chamber to evaporate water from the incubation mixture.

10. The method of claim 1, wherein said extracting a phytocannabinoid extract from the evaporated incubation mixture comprises:
   extracting residue from the evaporated incubation mixture using ethanol, olive oil, coconut oil, or hemp oil.

11. The method of claim 1, wherein said extracting a phytocannabinoid extract from the evaporated incubation mixture comprises performing a super critical $CO_2$ extraction.

12. The method of claim 1, comprising:
   performing vacuum distillation on the phytocannabinoid extract; or
   purifying the phytocannabinoid extract using preparative chromatographic separation.

13. The method of claim 12, wherein the preparative chromatographic separation comprises high performance liquid chromatographic separation.

14. The method of claim 1, wherein said extracting comprises performing microwave assisted extraction.

15. The method of claim 1, comprising:
   purifying the phytocannabinoid extract using preparative chromatographic separation.

16. The method of claim 15, wherein the preparative chromatographic separation comprises high performance liquid chromatography.

17. The method of claim 1, comprising:
   performing vacuum distillation on the phytocannabinoid extract.

* * * * *